(12) United States Patent
Becking et al.

(10) Patent No.: US 11,051,926 B2
(45) Date of Patent: *Jul. 6, 2021

(54) METHOD FOR RETRIEVAL OF A MEDICAL DEVICE

(71) Applicant: AVANTEC VASCULAR CORPORATION, Sunnyvale, CA (US)

(72) Inventors: Frank Becking, Los Gatos, CA (US); Nicholas DeBeer, Sunnyvale, CA (US); Karl Halden, Sunnyvale, CA (US); Teresa Ruvalcaba, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 112 days.

This patent is subject to a terminal disclaimer.

(21) Appl. No.: 16/007,740

(22) Filed: Jun. 13, 2018

(65) Prior Publication Data

US 2018/0289461 A1 Oct. 11, 2018

Related U.S. Application Data

(63) Continuation of application No. 14/569,500, filed on Dec. 12, 2014, now Pat. No. 10,022,213, which is a
(Continued)

(51) Int. Cl.
*A61F 2/01* (2006.01)
*A61B 17/221* (2006.01)
(Continued)

(52) U.S. Cl.
CPC .............. *A61F 2/01* (2013.01); *A61B 17/221* (2013.01); *A61F 2/013* (2013.01);
(Continued)

(58) Field of Classification Search
CPC ...... A61F 2/01; A61F 2/013; A61F 2002/011; A61F 2/011; A61F 2/9525; A61F 2/962; A61F 2002/9528; A61F 2002/9534
See application file for complete search history.

(56) References Cited

U.S. PATENT DOCUMENTS

| 3,952,737 A | 4/1976 | Kimmell, Jr. |
| 4,085,743 A | 4/1978 | Yoon |

(Continued)

FOREIGN PATENT DOCUMENTS

| EP | 1172073 A1 | 1/2002 |
| JP | H 10-509623 A | 9/1998 |

(Continued)

OTHER PUBLICATIONS

WO, PCT/US2015/058898 ISR and Written Opinion, dated Feb. 11, 2016.

(Continued)

*Primary Examiner* — Ashley L Fishback
(74) *Attorney, Agent, or Firm* — One LLP

(57) ABSTRACT

Funnel-trap type devices are described that are made of shape-set (e.g., heatset) braid for delivery and/or retrieval of Inferior Vena Cava (IVC) filters or other medical devices. Delivery and/or retrieval devices, kits in which they are included, methods of use and methods of manufacture are all contemplated. Additional forming tooling, methods and device embodiment shapes are described herein.

17 Claims, 5 Drawing Sheets

Related U.S. Application Data continuation-in-part of application No. PCT/US2014/042343, filed on Jun. 13, 2014.

(60) Provisional application No. 61/835,295, filed on Jun. 14, 2013.

(51) Int. Cl.
*A61M 25/00* (2006.01)
*A61B 17/22* (2006.01)
*A61F 2/95* (2013.01)

(52) U.S. Cl.
CPC . *A61M 25/0012* (2013.01); *A61B 2017/2215* (2013.01); *A61B 2017/22035* (2013.01); *A61F 2/011* (2020.05); *A61F 2002/016* (2013.01); *A61F 2002/9528* (2013.01); *A61F 2210/0014* (2013.01); *A61M 2025/0096* (2013.01)

(56) References Cited

U.S. PATENT DOCUMENTS

| | | |
|---|---|---|
| 4,174,715 A | 11/1979 | Hasson |
| 4,467,802 A | 8/1984 | Maslanka |
| 4,611,594 A | 9/1986 | Grayhack et al. |
| 4,655,219 A | 4/1987 | Petruzzi |
| 4,723,936 A | 2/1988 | Buchbinder et al. |
| 4,873,978 A | 10/1989 | Ginsburg |
| 4,960,411 A | 10/1990 | Buchbinder |
| 5,011,488 A | 4/1991 | Ginsburg |
| 5,041,093 A | 8/1991 | Chu |
| 5,074,845 A | 12/1991 | Miraki et al. |
| 5,098,440 A | 3/1992 | Hillstead |
| 5,102,415 A | 4/1992 | Guenther et al. |
| 5,370,647 A | 12/1994 | Graber et al. |
| 5,549,626 A | 8/1996 | Miller et al. |
| 5,601,595 A | 2/1997 | Smith |
| 5,653,684 A | 8/1997 | Laptewicz et al. |
| 5,662,671 A | 9/1997 | Barbut et al. |
| 5,746,251 A | 5/1998 | Bullard |
| 5,782,747 A | 7/1998 | Zimmon |
| 5,800,457 A | 9/1998 | Gelbfish |
| 5,814,064 A | 9/1998 | Daniel et al. |
| 5,827,324 A | 10/1998 | Cassell et al. |
| 5,846,251 A | 12/1998 | Hart |
| 5,908,435 A | 6/1999 | Samuels |
| 5,911,734 A | 6/1999 | Tsugita et al. |
| 5,944,728 A | 8/1999 | Bates |
| 6,001,118 A | 12/1999 | Daniel et al. |
| 6,152,946 A | 11/2000 | Broome et al. |
| 6,156,055 A | 12/2000 | Ravenscroft |
| 6,159,230 A | 12/2000 | Samuels |
| 6,203,561 B1 | 2/2001 | Ramee et al. |
| 6,210,370 B1 | 4/2001 | Chi-Sing et al. |
| 6,238,412 B1 | 5/2001 | Dubrul et al. |
| 6,241,738 B1 | 6/2001 | Dereume et al. |
| 6,251,092 B1 | 6/2001 | Qin et al. |
| 6,251,122 B1 | 6/2001 | Tsukernik |
| 6,264,671 B1 | 7/2001 | Stack et al. |
| 6,273,900 B1 | 8/2001 | Nott et al. |
| 6,290,710 B1 | 9/2001 | Cryer et al. |
| 6,306,163 B1 | 10/2001 | Fitz |
| 6,336,934 B1 | 1/2002 | Gilson et al. |
| 6,395,017 B1 | 5/2002 | Dwyer et al. |
| 6,443,972 B1 | 9/2002 | Bosma et al. |
| 6,447,531 B1 | 9/2002 | Amplatz |
| 6,458,151 B1 | 10/2002 | Saltiel |
| 6,485,501 B1 | 11/2002 | Green |
| 6,500,182 B2 | 12/2002 | Foster |
| 6,569,181 B1 | 5/2003 | Burns |
| 6,569,184 B2 | 5/2003 | Huter |
| 6,602,271 B2 | 8/2003 | Adams et al. |
| 6,605,102 B1 | 8/2003 | Mazzocchi et al. |
| 6,632,236 B2 | 10/2003 | Hogendijk |
| 6,645,222 B1 | 11/2003 | Parodi et al. |
| 6,663,652 B2 | 12/2003 | Daniel et al. |
| 6,679,893 B1 | 1/2004 | Tran |
| 6,695,813 B1 | 2/2004 | Boyle et al. |
| 6,699,260 B2 | 3/2004 | Dubrul et al. |
| 6,702,834 B1 | 3/2004 | Bpylan et al. |
| 6,743,247 B1 | 6/2004 | Levinson et al. |
| 6,780,196 B2 | 8/2004 | Chin et al. |
| 6,800,080 B1 | 10/2004 | Bates |
| 6,833,002 B2 | 12/2004 | Stack et al. |
| 6,896,690 B1 | 5/2005 | Lambrecht et al. |
| 6,958,074 B2 | 10/2005 | Russell |
| 7,211,089 B2 | 5/2007 | Kear et al. |
| 7,322,989 B2 | 1/2008 | Teague et al. |
| 7,338,512 B2 | 3/2008 | McGuckin, Jr. et al. |
| 7,377,925 B2 | 5/2008 | Poll |
| 7,491,210 B2 | 2/2009 | Dubrul et al. |
| 7,625,390 B2 | 12/2009 | Hendriksen et al. |
| 7,658,747 B2 | 2/2010 | Forde et al. |
| 7,731,723 B2 | 6/2010 | Kear et al. |
| 7,780,693 B2 | 8/2010 | Brady et al. |
| 7,780,694 B2 | 8/2010 | Palmer et al. |
| 7,837,702 B2 | 11/2010 | Bates |
| 7,993,362 B2 | 8/2011 | Lowe et al. |
| 8,038,704 B2 | 10/2011 | Sherburne |
| 8,043,322 B2 | 10/2011 | Hendriksen et al. |
| 8,163,004 B2 | 4/2012 | Amplatz et al. |
| 8,202,309 B2 | 6/2012 | Styrc |
| 8,273,073 B2 | 9/2012 | Levine et al. |
| 8,298,244 B2 | 10/2012 | Garcia et al. |
| 8,469,969 B2 | 6/2013 | Kear et al. |
| 8,469,970 B2 | 6/2013 | Diamant |
| 8,475,488 B2 | 7/2013 | Cartier et al. |
| 8,512,401 B2 | 8/2013 | Murray, III et al. |
| 8,747,597 B2 | 6/2014 | Rosqueta et al. |
| 8,795,305 B2 | 8/2014 | Martin et al. |
| 9,232,956 B2 | 1/2016 | Bonneau et al. |
| 9,949,816 B2 | 4/2018 | Becking et al. |
| 2001/0044595 A1 | 11/2001 | Reydel et al. |
| 2002/0010476 A1 | 1/2002 | Mulholland et al. |
| 2002/0062135 A1 | 5/2002 | Mazzocchi et al. |
| 2002/0068967 A1 | 6/2002 | Drasler et al. |
| 2002/0169474 A1 | 11/2002 | Kusleika et al. |
| 2002/0193827 A1 | 12/2002 | McGuckin et al. |
| 2003/0130680 A1 | 7/2003 | Russell |
| 2003/0176884 A1 | 9/2003 | Berrada et al. |
| 2003/0187474 A1 | 10/2003 | Keegan et al. |
| 2004/0049226 A1 | 3/2004 | Keegan et al. |
| 2004/0073230 A1 | 4/2004 | Mulholland et al. |
| 2004/0093012 A1 | 5/2004 | Cully et al. |
| 2004/0138677 A1 | 7/2004 | Little et al. |
| 2004/0153118 A1 | 8/2004 | Clubb et al. |
| 2004/0181237 A1 | 9/2004 | Forde et al. |
| 2004/0199202 A1 | 10/2004 | Dubrul et al. |
| 2005/0049576 A1 | 3/2005 | Snell et al. |
| 2005/0159770 A1 | 7/2005 | Divani et al. |
| 2005/0182439 A1 | 8/2005 | Lowe |
| 2005/0187570 A1 | 8/2005 | Nguyen et al. |
| 2005/0234502 A1 | 10/2005 | Gilson et al. |
| 2005/0251197 A1 | 11/2005 | Hensley et al. |
| 2005/0267515 A1 | 12/2005 | Oliva et al. |
| 2005/0283166 A1 | 12/2005 | Greenhalgh |
| 2006/0020256 A1 | 1/2006 | Bell et al. |
| 2006/0074410 A1 | 4/2006 | Malecki et al. |
| 2006/0074446 A1 | 4/2006 | Gilson et al. |
| 2006/0184193 A1 | 8/2006 | Lowe et al. |
| 2006/0247572 A1 | 11/2006 | McCartney |
| 2006/0259119 A1 | 11/2006 | Rucker |
| 2007/0005101 A1 | 1/2007 | Fahey et al. |
| 2007/0027520 A1 | 2/2007 | Sherburne |
| 2007/0112374 A1 | 5/2007 | Paul et al. |
| 2007/0129753 A1 | 6/2007 | Quinn et al. |
| 2007/0149996 A1 | 6/2007 | Coughlin |
| 2007/0162048 A1 | 7/2007 | Quinn et al. |
| 2007/0173884 A1 | 7/2007 | Gilson et al. |
| 2007/0186933 A1 | 8/2007 | Domingo et al. |
| 2007/0239254 A1 | 10/2007 | Chia et al. |
| 2007/0244504 A1 | 10/2007 | Keegan et al. |
| 2007/0282369 A1 | 12/2007 | Gilson et al. |
| 2008/0091223 A1 | 4/2008 | Pokorney et al. |

(56) References Cited

U.S. PATENT DOCUMENTS

| | | |
|---|---|---|
| 2008/0269774 A1 | 10/2008 | Garcia et al. |
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 | 9/2009 | Schneiderman |
| 2009/0222076 A1 | 9/2009 | Figulla et al. |
| 2009/0248060 A1 | 10/2009 | Schneider et al. |
| 2009/0287291 A1 | 11/2009 | Becking et al. |
| 2010/0030254 A1 | 2/2010 | Chanduszko et al. |
| 2010/0057184 A1 | 3/2010 | Randolph et al. |
| 2010/0137846 A1 | 6/2010 | Desai et al. |
| 2010/0256669 A1 | 10/2010 | Harris et al. |
| 2010/0312268 A1 | 12/2010 | Belson |
| 2010/0331949 A1 | 12/2010 | Habib |
| 2011/0040321 A1 | 2/2011 | Cartier |
| 2011/0046611 A1 | 2/2011 | Christiansen |
| 2011/0125180 A1 | 5/2011 | Tripp et al. |
| 2011/0178547 A1 | 7/2011 | Paul, Jr. et al. |
| 2011/0282274 A1 | 11/2011 | Fulton, III |
| 2011/0288572 A1 | 11/2011 | Martin |
| 2011/0307002 A1 | 12/2011 | Gilson et al. |
| 2012/0010699 A1 | 1/2012 | Vesely |
| 2012/0029607 A1 | 2/2012 | McHugo et al. |
| 2012/0041473 A1 | 2/2012 | Nigon |
| 2012/0089216 A1 | 4/2012 | Rapaport et al. |
| 2012/0123515 A1 | 5/2012 | Hosford et al. |
| 2012/0316638 A1 | 12/2012 | Grad et al. |
| 2013/0053882 A1 | 2/2013 | Hocking et al. |
| 2013/0131690 A1 | 5/2013 | Nagl et al. |
| 2013/0184738 A1 | 7/2013 | Laroya et al. |
| 2013/0197567 A1 | 8/2013 | Brady et al. |
| 2013/0253573 A1 | 9/2013 | Agnew |
| 2013/0267848 A1 | 10/2013 | Fearmot et al. |
| 2013/0289694 A1 | 10/2013 | Sherburne |
| 2013/0297010 A1 | 11/2013 | Bishop et al. |
| 2013/0317589 A1 | 11/2013 | Martin et al. |
| 2014/0005712 A1 | 1/2014 | Martin |
| 2014/0024887 A1 | 1/2014 | Ishii et al. |
| 2014/0155930 A1 | 6/2014 | Bennett et al. |
| 2014/0172008 A1 | 6/2014 | McKinnis et al. |
| 2014/0243878 A1 | 8/2014 | Urbanski et al. |
| 2014/0257362 A1 | 9/2014 | Eidenschink |
| 2014/0277089 A1 | 9/2014 | Goode et al. |
| 2014/0309656 A1 | 10/2014 | Gal et al. |
| 2014/0373334 A1 | 12/2014 | Gamarra et al. |
| 2015/0105819 A1 | 4/2015 | Becking et al. |
| 2015/0133918 A1 | 5/2015 | Sachar |
| 2015/0351775 A1 | 12/2015 | Fulton, III |
| 2015/0366650 A1 | 12/2015 | Zi et al. |
| 2016/0081704 A1 | 3/2016 | Jeon et al. |
| 2016/0095689 A1 | 4/2016 | Becking et al. |
| 2016/0095690 A1 | 4/2016 | Becking et al. |
| 2016/0166370 A1 | 6/2016 | DeBeer et al. |
| 2016/0296315 A1 | 10/2016 | Yachia et al. |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 A1 | 3/2000 |

OTHER PUBLICATIONS

WO, PCT/US2015/065074 ISR and Written Opinion, dated Mar. 22, 2016.

WO, PCT/US2015/065025 ISR and Written Opinion, dated Apr. 1, 2016.

JP, 2018-529531 Office Action, dated Sep. 19, 2019.

CN, 201580067678.4 First Office Action, dated Aug. 28, 2018.

CN, 201480084040.7 Second Office Action, dated Jun. 3, 2019.

EP, 16873911.8 Supplementary Search Report, dated May 2, 2019.

EP, 15910402.5 Supplementary Search Report, dated May 31, 2019.

JP, 2017-530585 Office Action, dated Jul. 16, 2019.

US, U.S. Appl. No. 15/847,473 Non-Final Office Action, dated Feb. 27, 2020.

EP, 14810754.3 Extended Search Report, dated Nov. 24, 2016.

EP, 14907807.3 Supplementary Search Report, dated May 15, 2018.

EP, 156867928.2 Supplementary Search Report, dated Jun. 5, 2018.

EP, 15867562.9 Supplementary Search Report, dated Jun. 5, 2018.

JP, 2016-519686 Official Action, dated Mar. 28, 2018.

US, U.S. Appl. No. 15/922,580 Non-Final Office Action, dated Jan. 27, 2020.

US, U.S. Appl. No. 15/989,845 Non-Final Office Action, dated Feb. 19, 2020.

WO, PCT/US2014/042343 ISR and Written Opinion, dated Sep. 30, 2014.

WO, PCT/US2015/065102 ISR and Written Opinion, dated Sep. 8, 2016.

WO, PCT/US2017/067343 ISR and Written Opinion, dated Mar. 22, 2018.

EP, 15867928.2 Supplementary Search Report, dated Jun. 5, 2018.

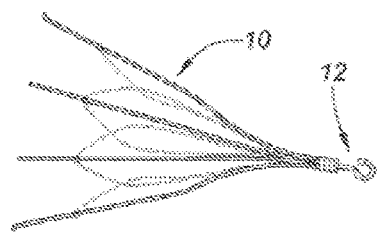
FIG. 1A
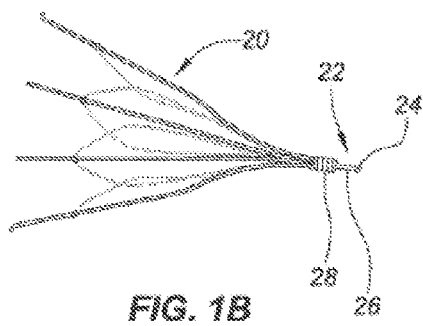
FIG. 1B
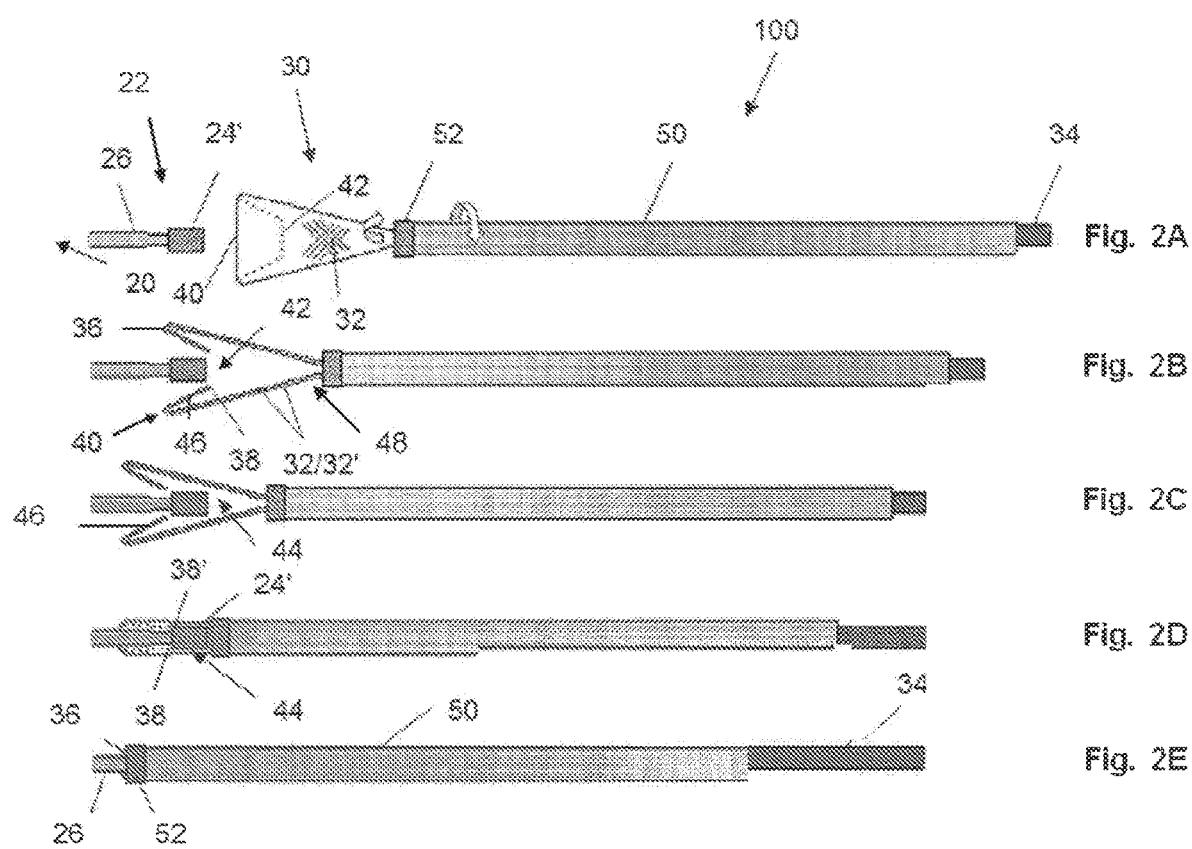

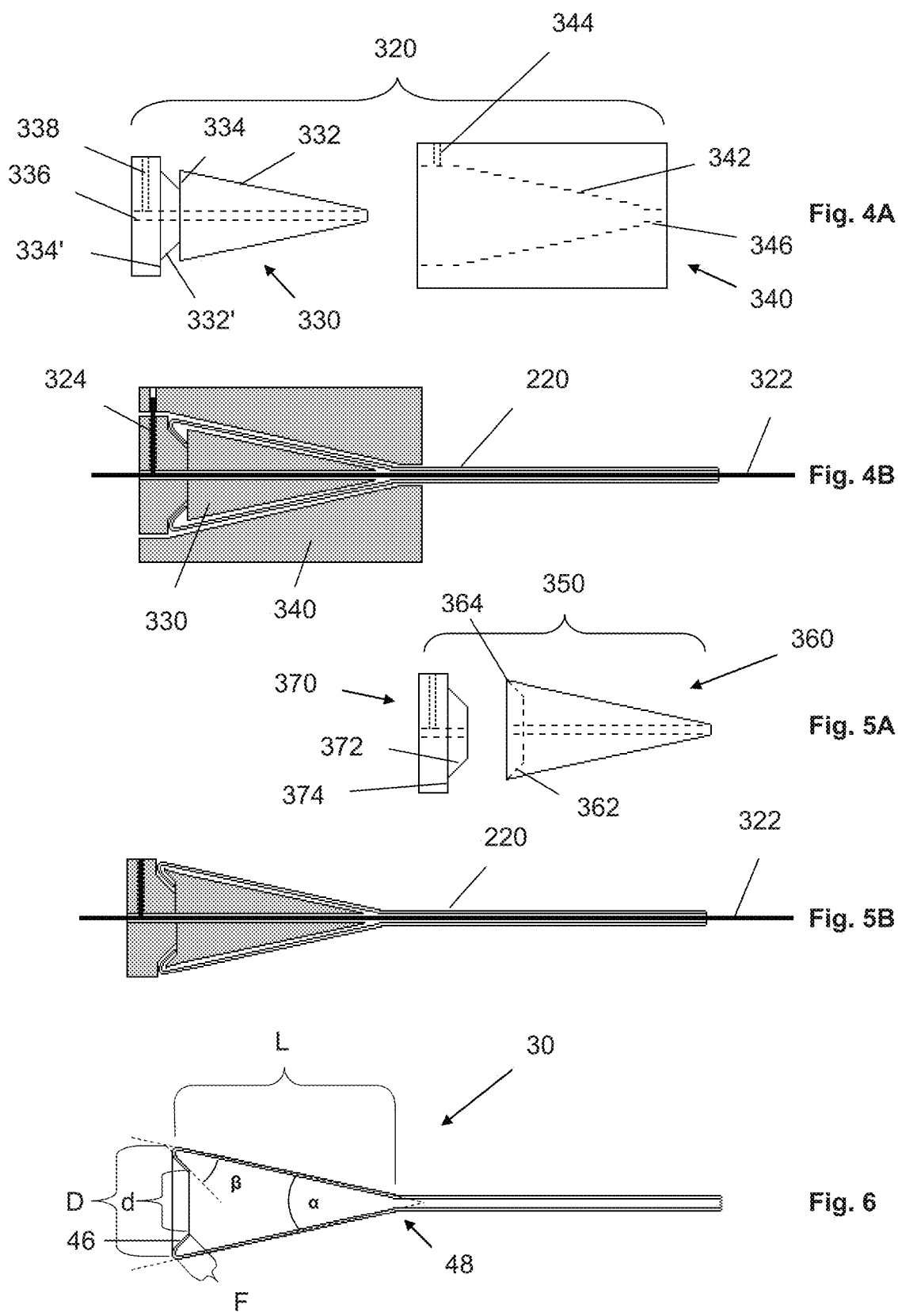

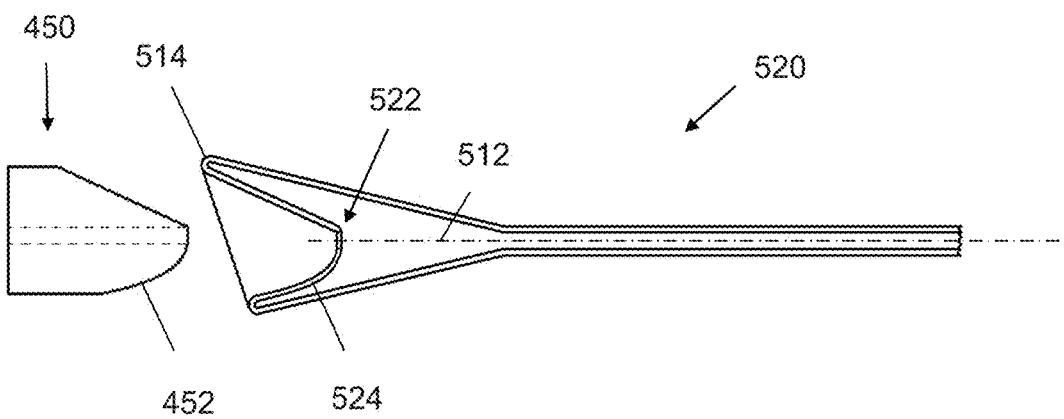
Fig. 10    Fig. 11
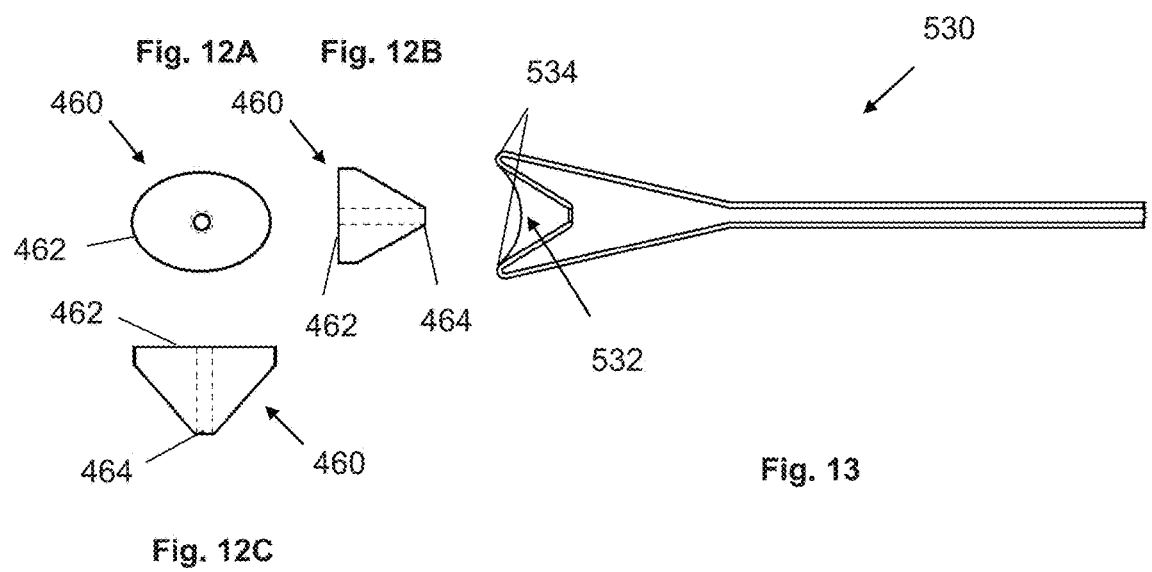

METHOD FOR RETRIEVAL OF A MEDICAL DEVICE

CROSS-REFERENCE TO RELATED APPLICATIONS

This application is a continuation of U.S. patent application Ser. No. 14/569,500, filed Dec. 12, 2014, which is a continuation-in-part of International Patent Application PCT/US2014/042343, filed Jun. 13, 2014, which claims priority to U.S. Provisional Application No. 61/835,295, filed Jun. 14, 2013, all of which are incorporated by reference herein in their entireties and for all purposes.

FIELD

The embodiments described herein relate to endovascular (percutaneously delivered) Inferior Vena Cava (IVC) filter or other implants, retrieval devices or system and methods.

BACKGROUND

Temporary IVC filters are placed much like permanent filters, but are designed so that they may be retrieved in a separate endovascular procedure, generally from a femoral vein or internal jugular vein approach. Most of the currently available temporary filters include a hook-like feature with which they can be captured and received within a catheter or sheath for removal by employing a gooseneck snare or a multi-loop snare.

While retrieval is a simple procedure in principle, difficulty is often encountered capturing a filter's hook with the snare loop(s). Such difficulty is compounded when the filter is tilted or off-kilter in placement. Several filters are designed to avoid such orientation. However, the problem remains common because the device is not anchored into the IVC in a stable fashion. Constant blood flow in addition to blood clots can disorient the filter within the IVC making recapture difficult.

Accordingly, there exists a need for a filter retrieval system with improved ease of use and/or less susceptibility to problems of filter orientation.

SUMMARY

The example embodiments provided herein meet this need and others as applied to other medical device applications. For IVC filters, the subject systems may be used with a wide variety of filter architectures—existing or otherwise. Accordingly, new filters may be designed for use with the subject retrievers in which fewer design constraints and/or compromises may be required of the filter design. Features of the subject system may be used in connection with existing and/or modified versions of the filters described in any of U.S. Pat. Nos. 3,952,747; 5,601,595; 6,443,972; 7,338,512 and 7,625,390 (all of which patents are incorporated herein by reference in their entireties for any purpose), commercially available devices including the OPTEASE, GUNTHER TULIP, CELECT and OPTION or others.

Example embodiments of the subject delivery and/or retrieval devices, kits in which they are included (with and without assembly), methods of use and manufacture (including assembly of the constituent components in vivo or ex vivo) are all included within the scope of the present disclosure.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 1A and 1B are photographs depicting example embodiments of IVC filters.

FIGS. 2A-2E are side views depicting an example embodiment of a delivery and/or retrieval system in various stages of action in connection with an end of any type of implantable medical device (IVC filter or otherwise).

FIG. 4A is a partial cross-sectional view depicting an example embodiment of tooling for converting the preform to a finally-shaped medical device; FIG. 4B is a partial cross-sectional view depicting an example embodiment of the tooling of FIG. 4A in use to shape an example embodiment of the medical device.

FIG. 5A is a partial cross-sectional view depicting another example embodiment of tooling for converting the preform to a finally-shaped medical device; FIG. 5B is a partial cross-sectional view depicting an example embodiment of the tooling of FIG. 5A in use to shape an example embodiment of the medical device.

FIG. 6 is a cross-sectional view depicting an example embodiment of a converted preform (i.e., a finally shaped funnel section of the subject device) after heatsetting.

FIG. 10 is a partial cross-sectional view depicting an example embodiment of an additional tool piece that may be used in conjunction with tooling like that of FIGS. 7A and 7B.

FIG. 11 is a cross-sectional view depicting an example embodiment of a preform that may be heatset using the tool piece of FIG. 10.

FIGS. 12A-12C are top, side, and front views, respectively, of an example embodiment of another tool piece that may be used in conjunction with tooling like that shown in FIGS. 7A and 7B.

FIG. 13 is a cross-sectional view depicting an example embodiment of a preform that may be heatset with tooling like that of FIGS. 12A-12C.

DETAILED DESCRIPTION

Figure 3A:
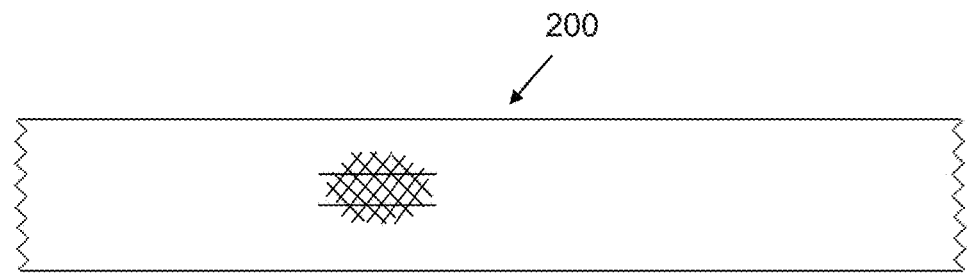
FIGS. 3A-3F are side and cross-sectional views depicting example embodiments of components used in the manufacture of a preform for constructing the subject retrieval system.

Before the present subject matter is described in detail, it is to be understood that this disclosure is not limited to the particular example embodiments described, as such may, of course, vary. It is also to be understood that the terminology used herein is for the purpose of describing particular embodiments only, and is not intended to be limiting, since the scope of the present disclosure will be limited only by the appended claims.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

FIG. 1A shows a GUNTHER TULIP (Cook Medical, Inc.) temporary IVC filter 10 with a hook 12 end interface for retrieval. As shown in FIG. 1B for an IVC filter 20, the hook may be modified or substituted for a nubbin-type interface 22. The nubbin (itself) may comprise a laser-formed or solder-formed protuberance or bump 24 on an extension 26 from a hub 28. Alternatively, as shown in FIGS. 2A-2E, the filter retrieval interface 22 may comprise a band 24' (e.g., a Pt marker band) mounted (e.g., by swaging, welding, gluing, etc.) on the extension 26. However, the enlargement is created, its interaction with the rest of the system will be apparent in the following figures.

Accordingly, FIG. 2A provides an overview of an example embodiment of the system 100. Here, a funnel-trap structure 30 made of braid material 32 is shown. It provides a flexible distal extension to an elongate shaft 34. The shaft is received within an elongate sleeve 50 (that may be a commercially available catheter or a custom part of the overall system 100) and may include a distal radiopaque marker band 52.

The braid may comprise Nitinol (preferably that is superelastic at body temperature), CoCr, Stainless Steel or another biocompatible material. It is advantageously braided material incorporating between 72 and 288 (more typically between 96 or 144 and 192) filament "ends" in a 1-over-1, a 2-over-2 or other maypole braided pattern. The braid may include so-called "axial" filaments as well. These may be used to improve column strength in a finally-formed device. The axial filaments may be incorporated in a/the maypole braided pattern when it is being formed or be added later manually. With (superelastic) Nitinol, the wire is advantageously between about 0.001 and about 0.003 inches in diameter. In which case, a supple and relatively "smooth" matrix surface is provided from which to construct the flexible funnel-trap architecture shown and described. The value of such a surface is in its atraumatic aspect and/or ability to help guide in IVC filter interface into position for capture even if it is oriented off-angle. Still, other wire size and/or end count in a braid or other construction options are possible as well. In alternative embodiments, non-braided materials are used.

To further assist with recapture, the funnel trap structure 30 may be selectably directable. As indicated by the arrows in FIG. 2A, the material from which it is made can be heatset or otherwise configured to provide a bias in an angular direction. The angle of deployment may be selectable or fully straightened by relative position of a core member or obturator (not shown) or by a sleeve or catheter sheath as further described. Further positioning may be achieved by rotating the device as further illustrated.

Other device articulation options for selecting the angular orientation of the subject funnel-trap portion of the device are possible as well. Any of a variety of steerable or directable catheter-type technologies (reliant on pull-wires or otherwise) can be incorporated in shaft 34 for such purposes. Examples include the mechanisms described in U.S. Pat. Nos. 4,723,936; 4,960,411; 6,251,092 and 8,273,073 each incorporated herein by reference in its entirety for such description.

In any case, FIG. 2B shows an advantageous construction of a braided multi-filar device in cross section. Here, inner and outer braid layers 32/32' are heatset using conventional techniques (e.g., in a furnace, salt pot, etc.) in a funnel shape with distal bends 36 in the braid wire forming an outer rim 40 with a large(r) distal opening and a meeting at inner bends 38 forming an inner rim 42 with a small(er) more proximal opening. Stated otherwise, the braid used to construct the funnel-shape trap is folded back (e.g., in a flap 46) at the distal opening to provide a more proximal opening.

This "funnel trap" may be generally frusto-conical as shown, tapered, flared or otherwise configured with a distal opening that is relatively larger than the proximal opening within the distal retrieval section. With an outer conical shape (i.e., triangular shape in cross section) the structure is highly supportive for any necessary or desirable tissue discretion that might need to occur to free an emplaced filter. Moreover, such a shape provides a flexible "waist" section 48 for the directable feature(s) noted above. Still, the device may be bowed outward along its sides or otherwise configured in alternative embodiments.

In many embodiments the distal rim opening 40 is larger than the more proximal rim opening 42 to operate as illustrated in guiding filter engagement feature(s) or enlargement 24/24' into a pocket 44 where it is captured and subsequently locked upon advancing sleeve 50 as shown in FIGS. 2D and 2E.

As shown, such a pocket 44 is formed between braid 32 walls and bend 38 ends optionally serving as an abutment feature with an optional shoulder 38' of nubbin/bump 24/24'. To ensure capture, the sleeve 50 may be advanced fully over trap 30 as shown in FIG. 2E before withdrawal into a separate catheter. In other words, advancing sleeve 50 over funnel section 30 "closes the trap" and securely captures the implant to be retrieved. Otherwise, the sleeve may be a catheter and shaft 34 withdraw continue until the implant (at left) is pulled therein as well. Any or all such activity may be visualized fluoroscopically by a physician by way of marker features 24/24' and 52 and/or others as may be conveniently provided. In alternative embodiments, the folded section can be omitted so long as the distal opening remains larger than the proximal opening and the trap functionality is retained.

Notably, system 100 may be used identically when capturing a filter 10 with a more typical hook end 12. However, the additional bulk/lateral extension of the hook may necessitate use of a relatively larger sleeve or catheter 50 than pictured in FIGS. 2A-2E.

In the various system architecture embodiments, the catheter/pusher shaft and/or sleeve may comprise a simple extrusion (e.g., PTFE, FEP, PEEK, PI, etc.) or may be constructed using conventional catheter construction techniques and include a liner, braid support and outer jacket (not shown), metal hypotube, etc. Further, the filter frame may be constructed using conventional laser cutting and electropolishing techniques and/or be otherwise constructed. In embodiments intended for tracking through a guide/delivery catheter without an incorporated sheath, a loading sheath may be employed. Advantageously, any such loading sheath is splittable. Other typical percutaneous access instruments (such as wires, etc.), valves and other hardware may also be employed in the embodiments.

The funnel-trap structure 30 may be made as a subassembly and attached to the catheter/pusher shaft. FIGS. 3A-3F detail optional steps in the manufacture of a pre-form for constructing the funnel-trap portion of the final device.

In FIG. 3A, a length or section 200 of braid as described above is provided. As shown, the braid pattern of crossing filaments may include interwoven angled elements as well as interwoven axial elements. The axial elements may comprise the same size and/or type of material (e.g., Nitinol) or more radiopaque material such at Pt, CoCr or Stainless Steel. As few as four axial members may be incorporated in the braid. More often six, eight or more such filaments are included. When axial filaments are employed which are smaller in diameter that the interwoven angular fibers, their number used may be greater. When relatively larger axial fibers are employed, the number used may be fewer. Regardless, the braid is advantageously heatset under tension upon the mandrel on which it was formed. As described by now-expired U.S. Pat. No. 6,447,531, such an approach enhances braid stability for subsequent device formation in further shape-setting of the device.

Figure 3B:
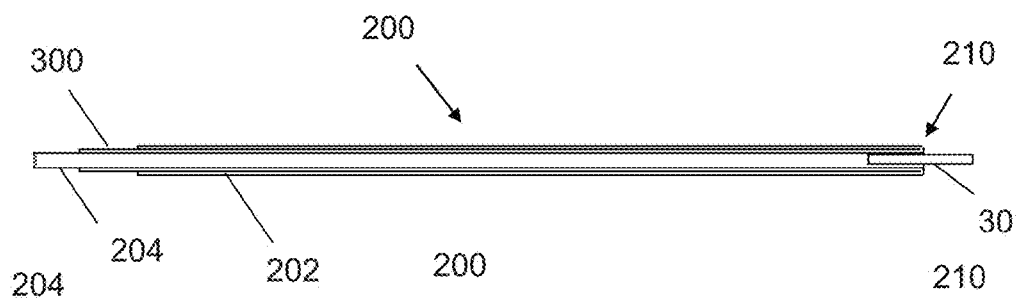

In FIG. 3B (a cross-section view), the braid section is shown doubled over a section hypotube 300. This may be accomplished by everting what is now an outer layer 202 of the braid 200 over the hypotube after feeding the inner layer 204 of braid there through. Alternatively, the inner layer may be fed into and through the hypotube after the outer layer is set over the hypotube. In any case, the braid wires are bent in a fold 210 at a distal end of the hypotube. Next, the braid is secured to the hypotube for heatsetting (e.g., at 520.degree. C. for 5 minutes for Nitinol braid). The braid may be secured by winding or wrapping with malleable wire or external forms (not shown) may be used to hold the braid relative to the hypotube for heatsetting. A press-fit rod or plug 301 may be used to secure and/or further compress the fold 210.

Figure 3C:
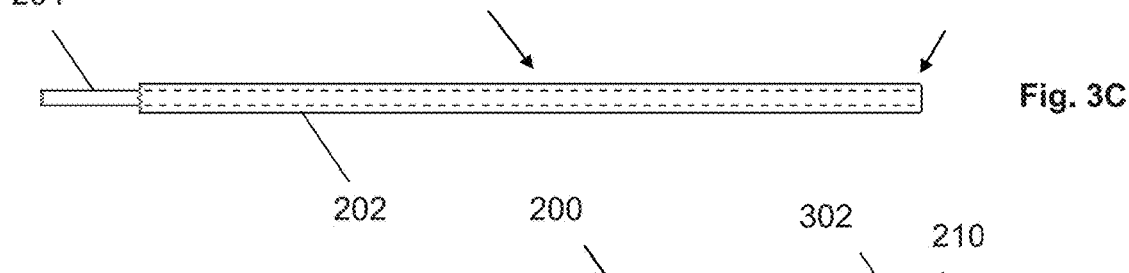
Figure 3D:
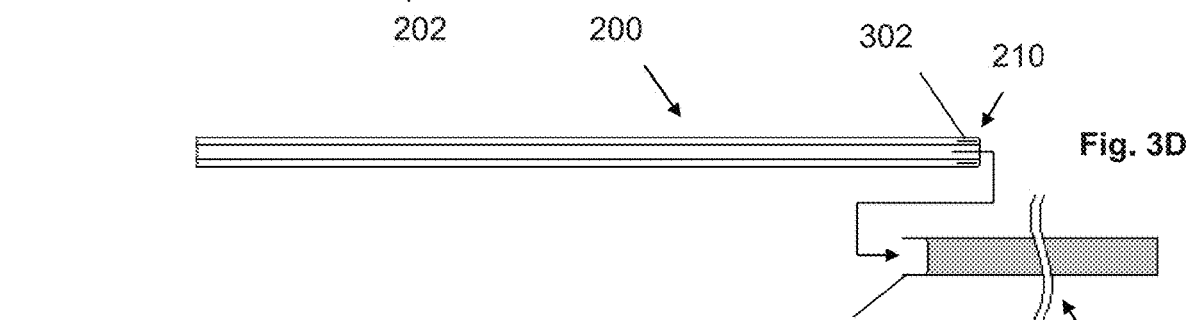

After heatsetting, the hypotube is removed as shown in FIG. 3C leaving only braid 200 in layers 202 and 204. As shown in FIG. 3D, the braid layers may be trimmed (e.g., with scissors) to the same length. In FIG. 3D (another cross-section view), a band 302 is inserted to abut the fold in the braid.

As with hypotube 300, band 302 preferably comprises strong material of minimal thickness. In each case, the structure is associated with forming bends in the braided wire. Thinner material will yield a tighter radius fold of the braid (or bend in the braid wires) as described. Advantageously, each of hypotube 300 and band 302 comprise superelastic Nitinol given that in the desired wall thickness (i.e., from about 0.001 to about 0.002 inches) such parts are tough and less prone to deformation and/or tearing as similarly-configured (otherwise usable) stainless steel, platinum or brass pieces.

Once prepared with band 302, the folded braid and band can be received within a pocket or socket 312 of a rod 310 or an end of another tube or hypotube. The pocket may offer a light press fit to the braid. Otherwise, the band-and-braid intermediate construction may be secured in socket 310 with glue (e.g., LOCTITE 4014).

Figure 3E:
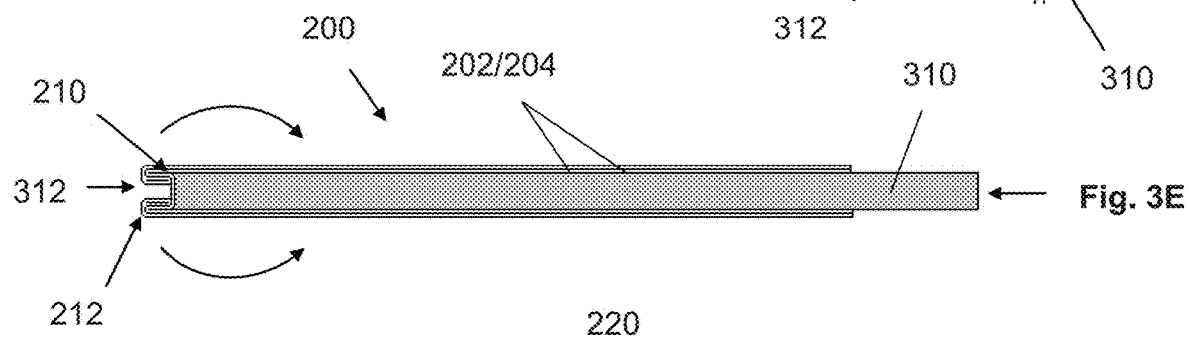
Figure 3F:

Then, both layers of braid 202/204 are flipped or everted over the rod and secured thereto (e.g., as by wrapping per above) as shown in FIG. 3E. So-fixtured, braid 200 includes a second fold 212 as shown in (cross-section view) FIG. 3E. Upon heatsetting (e.g., again, as per above), the fold(s) are set or fixed in shape. Then, the rod and band are removed providing a finished preform 220 as shown in FIG. 3F.

Such an approach to forming the bends 210/212 is advantageous in view of its simplified tooling. Further, the tooling used (i.e., bands and/or tubes) for this approach can be minimized in thickness to provide the tightest folds possible in the braid. As such, minimum diameter can be achieved for the compressed medical device as ultimately formed.

Regarding such formation (i.e., conversion from preform to final device configuration), FIG. 4A illustrates an example embodiment of a first set of tooling 320 that may be so-used. Toolset 320 includes an internal form or mandrel 330 and an external form 340 with cavity 342. These are shown in use relative to preform 220 in (cross-section view) FIG. 4B. With the braid so-positioned and secured over a rod 322 (e.g., tied-down as per above), optionally in connection with a setscrew 324, the braid is heated within the tooling construct to define a final funnel-trap device shape (e.g., as elaborated upon in connection with FIG. 6).

Notably, this final heatsetting cycle may take longer than previous cycles due to the thermal mass of the tooling. As such, it may be desirable to heat treat for approximately 10 minutes at temperature. Furthermore, it may be desirable to heatset in an inert atmosphere to minimize oxide formation. The same holds true for preceding heatsetting activities.

As for specific tooling features, mandrel 330 includes cone sections 332/332' and shoulder sections 334/334'. Together, these sections provide guidance for final device angular configuration and formation. A rod clearance hold 336 and a threaded setscrew hole 338 may also be provided in mandrel 330. External form 340 includes the aforementioned pocket 342 as well as optional setscrew and rod clearance holes 344 and 346, respectively.

External form 340 need not be used in shape-setting. However, its use/inclusion in the forming process may advantageously reduce part-to-part variability by further constraint in its application.

FIG. 5A illustrates an example embodiment of a second tooling approach for converting the preform 220 to a finally shaped device. Here, a two-part mandrel 350 is provided. It includes a cone piece 360 with an angled inset or pocket 362 that offers potential advantages by constraining the flap and fold 212 of the braid at rim or lip 364. An abutment piece 370 of tool 350 may be used to further constrain the braid. It includes a cone section 372 complementary to inset 362 and may also include a shoulder section 374 to further constrain or compress the braid during heatsetting. Together (or using cone piece 360, alone) the additional constraint in the fold and flap region—as compared to the configuration offered with mandrel 330—may obviate the need or advantage of using an external form like form 340 in the forming process such as shown in (cross-section view) FIG. 5B. Still, an external form (like form 340 shown in FIG. 4A) may be used in connection with tooling 350.

In general, the aforementioned forming methods are ones in which a heatset (possibly multiple-staged heatset) preform is provided that is substantially cylindrical in shape and includes an interior folded "flap" section. As such, the preform resembles the subject device in its fully compressed state for catheter tracking. Then, the preform is expanded (e.g., in a conical shape) to a desired "working" configuration and heatset accordingly.

Another forming and tooling approach may use thin-wall conical bands (not shown) in the shape-setting procedure. These may be used to directly shape or form the cone and flap sections of trap device 30. Such tooling may be constructed by "spinning" down thin-walled cylindrical material to the desired conical shapes and then trimming final pieces to length. However, use of internal tooling (as such) may limit the extent to which the braid layers lay in apposition after heatsetting, thereby resulting is some gap between the layers (i.e., unless the braid is subsequently formed with tooling as shown in FIGS. 4A/5A or otherwise).

Regardless of which tooling approach is employed, FIG. 6 illustrates a preform after conversion (or braid otherwise formed) to the subject funnel-trap device portion 30. For IVC filter retrieval, the funnel-trap portion 30 may have a diameter (D) from about 5 mm to about 20 mm, or more preferably about 10 to about 15 mm (i.e., size in a range to work within average size human IVCs where such vessels are reported as having a mean diameter of 20 mm within a range of 13 to 30 mm). A length (L) may range from about 10 mm to about 30 mm. An overall cone angle ($\alpha$) may be between about 30 and about 90 degrees. An angle ($\beta$) of flap 46 may be between about 0 and about 60 degrees and flap length (F) may be between about 1 and about 10 mm in length. Overall, a funnel trap opening diameter (d) may be between about 5 and about 95 percent of diameter (D) depending on the selected combination of the noted variables (i.e., d, D, L, F, $\alpha$ and ($\beta$). At the lower end of this range, the inner "opening" may be substantially closed such that is must be pushed-open to receive the proximal engagement feature(s) of the implant during retrieval. At the higher end of the range, the flap may lie completely along or in-line with the outer layer(s) of the device.

Figure 7A:
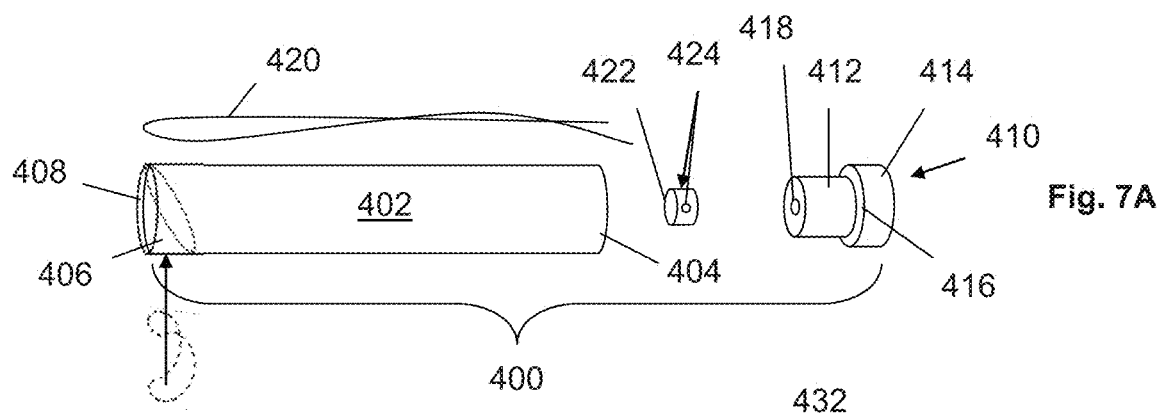
FIG. 7A is a partial cross-sectional view depicting another example embodiment of tooling for converting the preform to a finally-shaped medical device.
Figure 8:
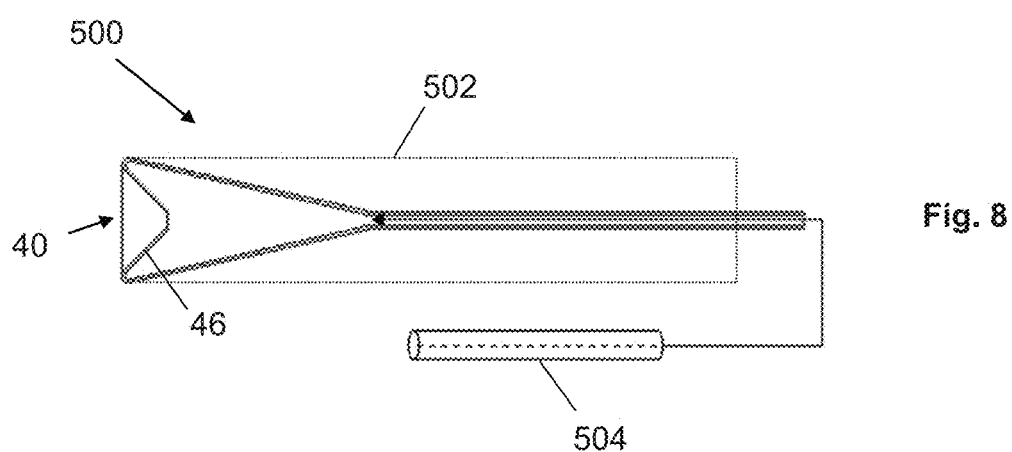
FIG. 8 is a partial cross-sectional view depicting an example embodiment of a medical device after its preform is heatset with tooling like that of FIGS. 7A and 7B.

FIG. 7A illustrates another example embodiment for converting the shape of a preform. Namely, tooling 400 is used to produce a second or secondary preform shape 500 as shown in FIG. 8 and further described below.

The tooling or toolset 400 includes a cylindrical shell or tube 402. A plug 410 is provided for its proximal end 402. A distal end 406 of the tube may be cut at 90 degrees or at an angle (see dashed profile) relative to an axis (not shown). Alternatively, an undulating or saddle-shaped profile may be substituted therefore as indicated.

In any case, the end may be formed as a sharpened edge 408 (e.g., using a counter bore, de-burring tool or otherwise). Plug 410 includes inner and outer cylinder sections 412, 414. Inner section 412 is sized to fit within tube 402 with a shoulder 416 of the plug abutting the tube. Plug 410 also includes a through hole 418 to accommodate wire 420. Wire 420 may also pass through a band 422 through apertures 424.

Figure 7B:
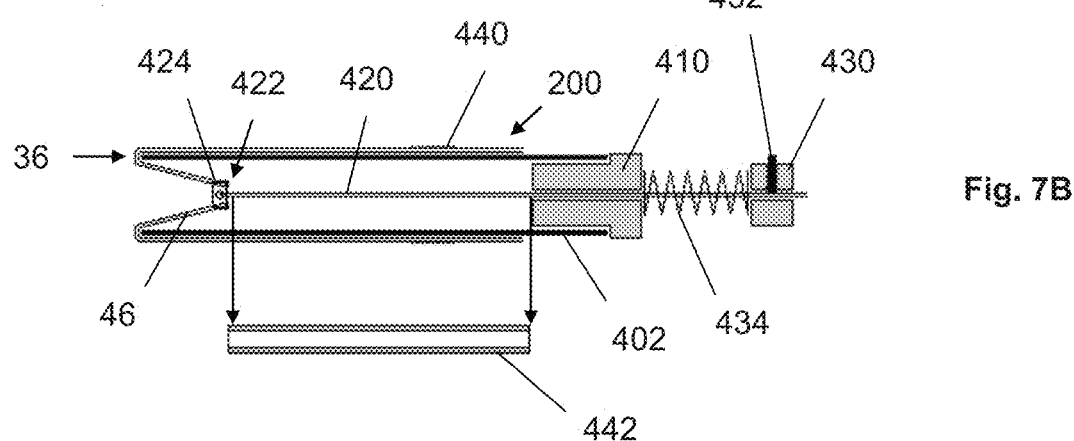
FIG. 7B is a partial cross-sectional view depicting an example embodiment of the tooling of FIG. 7A in use to shape an example embodiment of the medical device.

Such an arrangement is shown in FIG. 7B. Specifically, wire 420 is looped and passes through apertures 424 in band 422 and proximally through plug 410. At or near a proximal end of the wire, a boss 430 with a set screw 432 secures the wire under tension applied by a spring 434. A coil spring is shown, although various leaf spring or spring washer arrangements may alternatively be used.

In any case, spring tension is held at the opposite end of the wire by the braid 200 in which band 422 is captured. The braid is folded over tube 402 to form its distal bend 36 and secured to the tube with a wire wrap 440 or other clamping mechanism. In setting up the distance between the proximal side of band 422 (together with associated flap 46) a sizing tube 442 may be temporarily interposed as shown and removed prior to inserting plug 430 into tube 402 and tensioning wire 420 and braid 200.

Once heatset, the product (i.e., the second or secondary shape preform 500) appears with a cylindrical outer body 502 and an angled interior flap 46 as indicated in FIG. 8. Once a heat shrink sheath 504 or other constraint is applied thereto, the device takes its final shape and is ready for mounting on a catheter or pusher body as the funnel trap portion of the overall device.

The shaping sheath 504 may be permanently included in the final construction (i.e., form part of the product's catheter shaft or pusher) or it may be temporarily used in a heatsetting procedure to finally shape the device. Alternatively, a wire wrap (not shown) may be used to effect an additional heatsetting cycle to finalize the shape.

The ultimate cross-sectional profile may appear as it does in FIG. 8 with a face or opening 40 set at 90 degrees relative to an axis defined by the body of the device. Alternatively, the opening may be as shown in funnel trap portion 510 in FIG. 9 where it is angled relative to such an axis 512 of the body by an acute angle y. In which case, the angle may advantageously range from about 45 to about 60 degrees.

A face or opening 40 so-angled provides a leading edge 514 for picking-up IVC filter hooks and/or nubs adjacent the vessel wall. The shape may help when rotating the body of the retrieval device into such a target structure or anatomy, or be otherwise employed. Moreover, the various directional or directable aspects of the system(s) described above may be so-employed.

Figure 9:
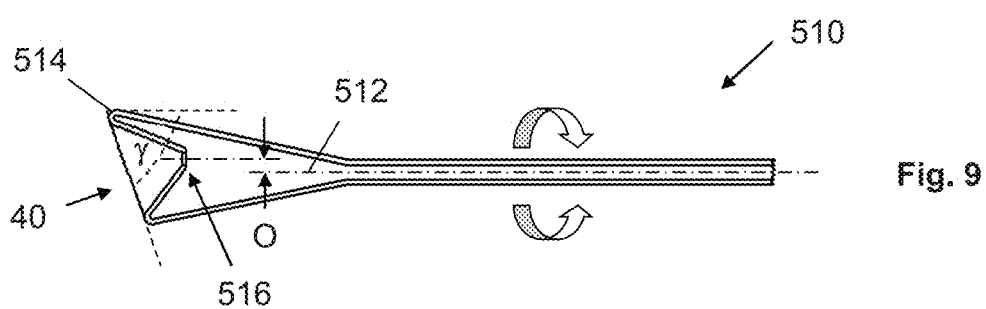
FIG. 9 is a cross-sectional view depicting an example embodiment of a preform set in a different shape using the tooling like that of FIGS. 7A and 7B.

In forming a device portion or preform with an angled distal end (e.g., as shown in FIG. 9), the proximal aperture or opening 516 may be set at and offset distance "O" in order to take-up slack that would otherwise be present in the braid when heatsetting the angled shape. Removing the slack in the braid (as such) enables uniform tensioning of the braid in forming a tight distal crease or fold around over angled tooling edge 408 (e.g., as in tooling 400 shown in FIGS. 7A and 7B).

FIG. 10 illustrates an example embodiment of another heat setting form or tool piece 450 that may be used in conjunction with tooling 400. By its use, a funnel trap section 520 can be formed as shown in FIG. 11. The complimentary nature of the shapes illustrated is apparent.

More specifically, a/the proximal aperture or opening 522 is centered. To allow for this, a shoulder or arch portion 452 of tool 450 is used to deform and tighten the braid of the funnel trap over a complimentary arc 524 along its down-angle side. Tool 450 is simply used in line with wire 420, band 422, boss 430 and the other tooling shown in FIG. 7B to create such a heatset in the braid.

FIG. 12A-12C shows views of an example embodiment of another tool piece 460 used for braid tensioning to account for shell 402 edge asymmetry. A preform conversion or final funnel trap section 530 with a tight distal fold or crease around a "fishmouth" or "saddle" shape distal opening or end 532 can be produced in connection with such a tool piece or form. In which case, shell 402 is configured with the saddle-shaped profile shown in FIG. 7A.

So-formed, funnel trap section 530 includes two protruding curved lips, edges or ridges 534 (as compared to having one leading edge or ridge 514 as in the variations shown in FIGS. 9 and 11). Such a shape may be advantageous in reducing procedural complexity and any necessary rotation in securing the end of a filter.

Forming such a complex shape can be challenging. Yet, tool piece 460 with its biased shape (i.e., tapered from an oval or elliptical base 462 to a circular cross-section end or tip 464) enables a taught fit of the braid from which the device is made over the saddle-shaped edge of shell 402. As such, a tightly creased rim or edge can be effectively heatset in the braid at the distal end of the device.

In each example of a device section 520 and 530, the braid is formed with a tool (450, 460) in the form of a plug that asymmetrically tensions or loads the braid. The asymmetry in the plug and/or the braid tensioning enables centering the proximal aperture of the funnel trap device for IVC filter hook or nub capture. Other uses of the technique may be possible as well.

All of the embodiments described herein are freely interchangeable. For example, all of the example embodiments of filters can be used with all of the embodiments of the delivery or retrieval devices and all of the example embodiments of the delivery or retrieval devices can be manufactured with all of the example embodiments of manufacturing tooling and manufacturing steps as described or with minor modifications that would be evident to those of ordinary skill in the art upon review of this disclosure.

Variations

The subject methods, including methods of use and/or manufacture, may be carried out in any order of the events which is logically possible, as well as any recited order of events. Medical methods may include any of a hospital staff's activities associated with device provision, implant positioning, re-positioning, retrieval and/or release.

Furthermore, where a range of values is provided, it is understood that every intervening value, between the upper and lower limit of that range and any other stated or intervening value in the stated range is encompassed within the disclosure. Also, it is contemplated that any optional feature of the embodiments described may be set forth and claimed independently, or in combination with any one or more of the features described herein.

Reference to a singular item includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Accordingly, the breadth of the different embodiments or aspects described herein is not to be limited to the examples provided and/or the subject specification, but rather only by the scope of the issued claim language.

The invention claimed is:

1. A method for delivery or retrieval of a medical device, the method comprising:
   passing an elongate shaft having a longitudinal axis through a body lumen of a subject, the shaft having a flexible distal extension folded back at a first fold to form two layers, the two layers folded back inwardly at a second fold such that the first fold is a proximal opening of a funnel and the second fold is a distal opening of the funnel, wherein the distal opening is configured to have a saddle shape cross section and to be set at an acute angle relative to the axis of the shaft upon deployment; and
   passing an end portion of the medical device through the distal opening and then through the proximal opening of the funnel to capture the medical device.

2. The method of claim 1, wherein the distal extension comprises heatset Nitinol braid with between 72 and 288 end count.

3. The method of claim 2, wherein the shaft includes the Nitinol braid.

4. The method of claim 1, wherein the distal extension has an exterior conical shape.

5. The method of claim 1, wherein the acute angle is between about 45 and about 60 degrees.

6. The method of claim 1, further comprising covering the medical device with an elongate sleeve.

7. The method of claim 6, wherein the elongate sleeve is a catheter.

8. The method of claim 6, wherein the distal opening is configured to close and trap the end portion of the medical device within the distal extension when covered by the elongate sleeve.

9. The method of claim 8, wherein the proximal opening is configured to close and trap the end portion of the medical device within the distal extension when covered by the elongate sleeve.

10. The method of claim 6, wherein the elongate sleeve is advanced to cover the medical device.

11. The method of claim 10, wherein medical device is withdrawn through the elongate sleeve after the elongate sleeve is advanced.

12. The method of claim 6, wherein a portion of the medical device is captured in a pocket of the distal extension by covering with the sleeve.

13. The method of claim 1, wherein a portion of the proximal opening is at least partially closed to capture the medical device.

14. The method of claim 13, wherein the proximal opening is at least partially closed by retracting a tether.

15. The method of claim 1, wherein the medical device includes a hook and the hook is captured at the proximal aperture.

16. The method of claim 15, wherein the hook engages at least one of a rim or an aperture crossing member at the proximal opening for capture.

17. The method of claim 1, wherein the proximal opening is sized to receive and pass an end portion of the medical device to situate and secure the end portion of the medical device within the flexible distal extension when the sleeve is advanced over the distal extension.

\* \* \* \* \*